US00PP13894P29

(12) United States Plant Patent
van Winsen

(10) Patent No.: US PP13,894 P2
(45) Date of Patent: Jun. 17, 2003

(54) ECHINACEA PLANT NAMED 'RAZZMATAZZ'

(75) Inventor: Johannes Matthias van Winsen, Warmond (NL)

(73) Assignee: Witteman & Co. 'Multiflora' B.V., Hillegom (NL)

( * ) Notice: Subject to any disclaimer, the term of this patent is extended or adjusted under 35 U.S.C. 154(b) by 42 days.

(21) Appl. No.: 10/139,964

(22) Filed: May 6, 2002

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,242 P2 * 12/2001 Hawks ..... Plt./263

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Echinacea plant named 'Razzmatazz', characterized by its upright plant habit; anemone-type inforescence form; and dark pink-colored ray florets and enlarged red purple-colored disc florets.

1 Drawing Sheet

BOTANICAL CLASSIFICATION/CULTIVAR DESIGNATION

*Echinacea purpurea* cultivar Razzmatazz.

BACKGROUND OF THE INVENTION

The present Invention relates to a new and distinct cultivar of Echinacea plant, botanically known as *Echinacea purpurea*, and hereinafter referred to by the name 'Razzmatazz'.

The new Echinacea was discovered as a naturally-occurring whole plant mutation of an unidentified selection of *Echinacea purpurea*, not patented. The Inventor discovered and selected the new Echinacea as a single flowering plant within a population of plants of the unidentified Echinacea selection in 1997 in a controlled environment in Warmond, The Netherlands.

Asexual reproduction of the new Echinacea by cuttings was first conducted in Warmond, The Netherlands in 1998. Since then, asexual reproduction by cuttings has shown that the unique features of this new Echinacea are stable and reproduced true to type in successive generations.

SUMMARY OF THE INVENTION

The cultivar Razzmatazz has not been observed under all possible environmental conditions. The phenotype may vary somewhat with variations in environment such as temperature and light intensity without, however, any variance in genotype.

The following traits have been repeatedly observed and are determined to be the unique characteristics of 'Razzmatazz'. These characteristics in combination distinguish 'Razzmatazz' as a new and distinct Echinacea:

1. Upright plant habit.

2. Anemone-type inflorescence form.

3. Dark pink-colored ray florets and enlarged red purple-colored disc florets.

Plants of the new Echinacea differ primarily from plants of the parent selection in inflorescence form and ray and disc floret coloration.

Plants of the new Echinacea can be compared to plants of the Echinacea cultivar Magnus, not patented. Plants of the new Echinacea have anemone-type inflorescences whereas plants of the cultivar Magnus have daisy-type inflorescences. In addition, plants of the new Echinacea and the cultivar Magnus differ in ray and disc floret coloration.

BRIEF DESCRIPTION OF THE PHOTOGRAPH

The accompanying colored photograph illustrates the overall appearance of the new Echinacea showing the colors as true as it is reasonably possible to obtain in colored reproductions of this type. Colors in the photograph may differ from the color values cited in the detailed botanical description which accurately describe the colors of the new Echinacea. The photograph comprises a side perspective view of a typical flowering plant of 'Razzmatazz' grown in an outdoor nursery.

DETAILED BOTANICAL DESCRIPTION

The aforementioned photograph and following observations and measurements describe plants grown in Warmond, The Netherlands, in an outdoor nursery under full sun conditions. During the summer, when plants were about one year old, the photograph and the observations and measurements were taken. Color references are made to The Royal Horticultural Society Colour Chart, 2001 edition, except where general terms of ordinary dictionary significance are used.

Botanical classification:
*Echinacea purpurea* cultivar Razzmatazz.
Parentage: Naturally-occurring whole plant mutation of an unidentified selection of *Echinacea purpurea*, not patented.

Propagation:

*Type.*—By cuttings.

*Time to produce a rooted plant.*—About 40 days.

*Root description.*—Fine, fibrous and well-branched.

Plant description:

*Appearance.*—Perennial herbaeceous container and garden plant. Upright plant habit; narrow inverted triangle. Not freely branching; about four to six basal branches; pinching required for lateral branch development. Moderately vigorous growth habit.

*Plant height.*—About 80 cm.

*Plant width or area of spread.*—About 50 cm.

*Basal branches.*—Length: About 80 cm. Diameter: About 4 mm. Internode length: About 6 cm. Aspect: Mostly upright. Strength: Strong. Texture: Sparsely pubescent; rough. Color: 144B to 144C.

*Foliage description.*—Arrangement: Alternate; single. Length: About 13 cm. Width: About 8 cm. Shape: Ovate. Apex: Acuminate. Base: Attenuate to cuneate. Margin: Entire or irregularly serrate. Venation pattern: Pinnate. Texture, upper and lower surfaces: Pubescent; rough. Color: Young and fully expanded foliage, upper surface: 137A. Young and fully expanded foliage, lower surface: 137C. Venation, upper and lower surfaces: 144C to 144D. Petiole: Length: About 20 cm. Diameter: About 2 mm. Texture, upper and lower surfaces: Smooth. Color, upper and lower surfaces: 144A to 144B.

Inflorescence description:

*Appearance.*—Terminal and axillary inflorescences held mostly above and beyond the foliage on strong peduncles. Composite anemone inflorescence form, radially symmetrical; oblanceolate to oblong-shaped ray florets; enlarged disc florets massed at the center; ray and disc florets arranged acropetally on a capitulum. Inflorescences persistent. Inflorescences face mostly upright.

*Flowering response.*—Plants flower continuous and freely from late July into September in Warmond, The Netherlands.

*Postproduction longevity.*—Inflorescences maintain good color and substance for about two weeks on the plant or as a cut flower.

*Quantity of inflorescences.*—About one inflorescence per stem, about four to six open inflorescences per plant at one time.

*Fragrance.*—Faint, sweet.

*Inflorescence bud* (*at stage of showing color*).—Length: About 2.2 cm. Diameter: About 3.2 cm. Shape: Narrowly ovoid. Color: 175A.

*Inflorescence size.*—Diameter: About 8 cm. Depth (height): About 6 cm. Disc diameter: About 5 cm.

*Ray florets.*—Length: About 3.7 cm. Width: About 1 cm. Shape: Oblanceolate to oblong. Apex: Emarginate to praemorse. Base: Acute. Margin: Entire. Texture, upper surface: Smooth. Texture, lower surface: Sparse pubescence. Orientation: Initially upright then perpendicular to the peduncle; with development, ray florets reflexed. Number of ray florets per inflorescence: About 15 in one whorl. Color: When opening, upper and lower surfaces: 70C. Fully opened, upper surface: 64B. Fully opened, lower surface: 64A to 64B.

*Disc florets.*—Shape: Enlarged, elongated. Apex: Five-pointed; acute. Length: About 2 cm. Width: About 5 mm. Number of disc florets per inflorescence: About 275. Color When opening, throat: 58B. When opening, tube: 58B with longitudinal stripes, 62C. Fully opened, throat: 58A to 58B. Fully opened, tube: 58A to 58B with longitudinal stripes, 62C to 62D.

*Phyllaries.*—Length: About 6 mm. Diameter: About 2 mm. Shape: Narrowly ovate to lanceolate. Apex: Acute. Base: Fused. Margin: Enitre. Texture: Densely pubescent. Number per inflorescence: About 50 in about five or six whorls. Color, upper surface: 143B. Color, lower surface: 143A.

*Peduncles.*—Length: About 15 cm. Diameter: About 3 mm. Angle: Mostly erect. Strength: Strong. Texture: Sparsely pubescent; rough. Color: 144B to 144C.

*Reproductive organs.*—Androecium: Present on disc florets only. Stamen number: About four per floret; basifixed. Anther shape: Narrowly oblong. Anther length: About 1 mm. Anther color: Close to 199B. Pollen amount: Scarce. Pollen color: 17B to 17C. Gynoecium: Present on both ray and disc florets. Pistil number: One per floret. Pistil length: About 5 mm. Stigma shape: Two-parted. Stigma color: 187A. Style length: About 4 mm. Style color: 187B. Ovary color: 150D to 157A.

*Seed/fruit.*—Seed nor fruit production has been observed.

Disease/pest resistance: Resistance to pathogens and pests common to Echinaceas has not been observed on plants grown under outdoor conditions.

Temperature tolerance: Plants of the new Echinacea have been observed to tolerate temperatures from about −12 to 35° C.

It is claimed:

1. A new and distinct cultivar of Echinacea plant named 'Razzmatazz', as illustrated and described.

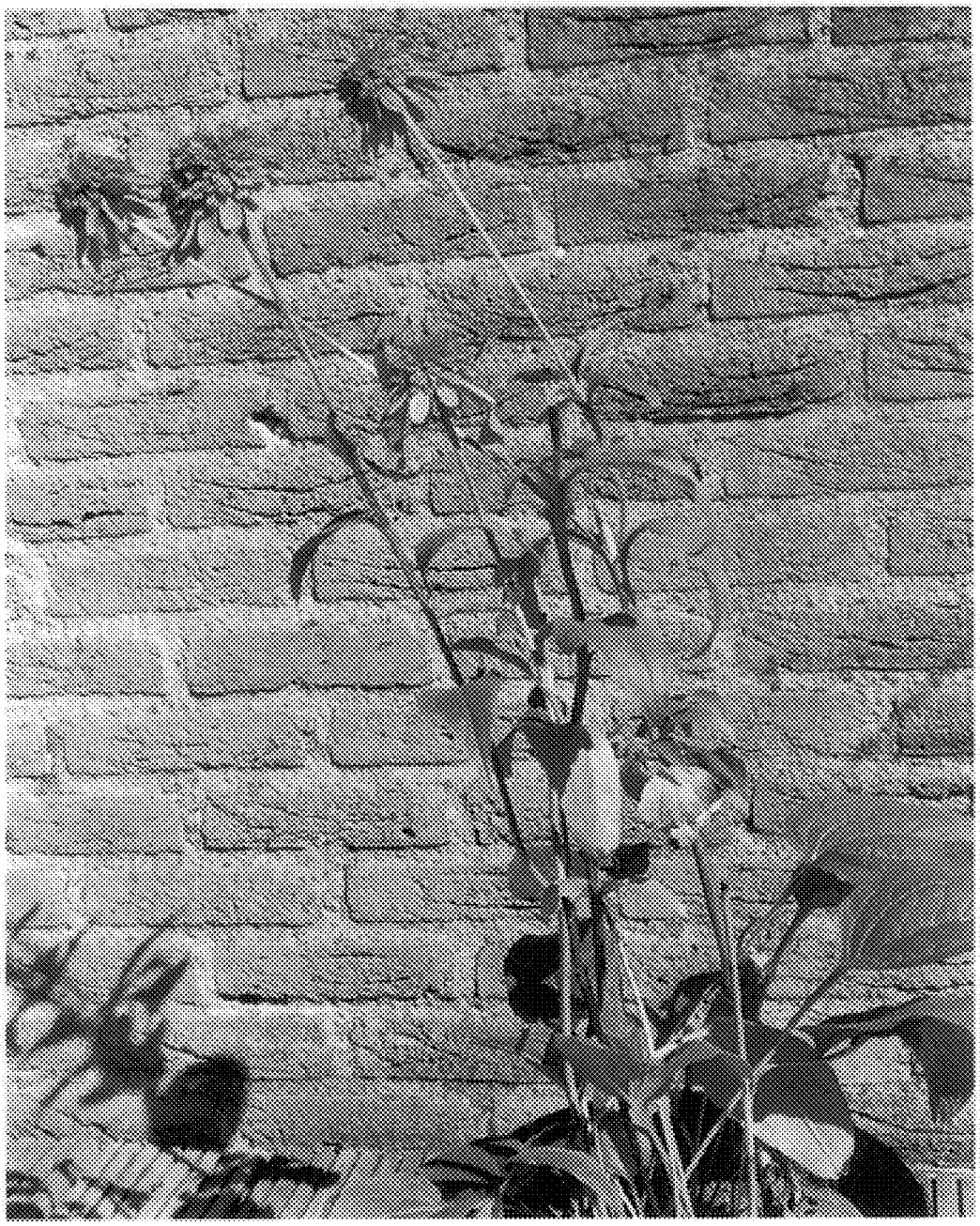

* * * * *